United States Patent [19]

Gupte et al.

[11] Patent Number: 4,778,674

[45] Date of Patent: Oct. 18, 1988

[54] DRY AEROSOL FOAM

[75] Inventors: Anil J. Gupte, Seymour; Rodger E. Bogardus, Trumbull, both of Conn.

[73] Assignee: Richardson-Vicks Inc., Wilton, Conn.

[21] Appl. No.: 867,508

[22] Filed: May 28, 1986

[51] Int. Cl.[4] .......................... A61L 9/04; A61K 7/15
[52] U.S. Cl. ........................................ 424/45; 424/46; 424/65; 424/73; 424/47; 514/770
[58] Field of Search ..................... 424/45, 46; 514/770

[56] References Cited

U.S. PATENT DOCUMENTS

| 4,108,984 | 8/1978 | Sato | 424/94 |
| 4,122,159 | 10/1978 | Mandrange et al. | 424/45 |
| 4,574,052 | 3/1986 | Gupte et al. | 252/90 |

Primary Examiner—Leonard Schenkman
Attorney, Agent, or Firm—Salvatore R. Conte; David K. Dabbiere; Douglas C. Mohl

[57] ABSTRACT

A pressurized aerosol composition containing zeolite, surfactant, water and propellant in prescribed amounts and ratios which, upon discharge from an aerosol container, produces a characteristically dry foam.

10 Claims, No Drawings

DRY AEROSOL FOAM

FIELD OF THE INVENTION

This invention relates to an aerosol foamable composition which produces a light, dry, fluffy foam when discharged through aerosol containers. The foam eventually collapses to a powder.

BACKGROUND OF THE INVENTION

Aerosol personal products are an important segment of the toiletries and cosmetic industry. It has long been recognized as desirable to provide various types of aerosol products such as, for example, hair sprays, antiperspirants and deodorants, shaving lathers, colognes and perfumes, medicinal and pharmaceuticals, etc. Such aerosol products include the propulsion, or dispensing from aerosol containers of so-called micronized or atomized mists in liquid or solid form. Of particular interest with regard to the subject invention, however, are pressurized foamable products which provide a foam, rather than a mist, when discharged through aerosol containers. A particularly well known class of pressurized foam products are those made by incorporating an aqueous soap solution or a liquid detergent in a liquified gas propellant, for example, shaving lathers. The thus obtained foams are characteristically moist due to their inherent water content.

It would therefore be highly desirable to be able to provide pressurized foamable products which produce foams which are particularly characterized by a pronounced dryness to the touch despite a relatively high water content.

SUMMARY OF THE INVENTION

It has been found that a composition comprising, as its essential components, from about 14 to about 40 percent by weight zeolite (molecular sieve), from about 0.5 to about 13 percent by weight surfactant, from about 32 to about 55 percent by weight water and from about 10 to about 35 percent by weight liquified gas propellant, wherein the ratio of zeolite to water is from about 1:1 to about 1:2.75, the ratio of zeolite to surfactant is from about 1:0.035 to about 1:0.65 and the ratio of zeolite to propellant is from about 1:0.43 to about 1:1.16, when dispensed from an aerosol container produces a foamed composition which is characterized by a pronounced feeling of dryness.

In U.S. Pat. No. 4,574,052, a pressurized foamable composition is disclosed which produces a crackling sound upon discharge, such composition containing zeolite, surfactant and a liquified gas propellant. It also contains as an essential ingredient a non-aqueous vehicle, specifically an alkylene glycol, polyalkylene glycol or vegetable oil, and the resultant crackling foam has an oily, greasy appearance and feel. In contrast, the compsitions of the subject invention are devoid of such non-aqueous vehicles, utilizing water as the sole vehicle, and the resultant foam is characteristically dry in appearance and feel.

When the pressure in a pressurized aerosol container of this invention is released by means of a valve on the aerosol container the contents of this pressurized container are discharged and the liquified gas propellant which is discharged from the container vaporizes substantially instantaneously and forms a foam of the contents as the contents of the aerosol container enter the lower pressure zone of the atmosphere. Notwithstanding the relatively high water percentage of said contents, the resultant foam is surprisingly dry to the touch, and the foam eventually crumbles to a dry powder. If rubbed or smeared before collapsing, a fine powdery film is left on the surface. It is believed that the dry characteristic of the foam is due to the high adsorptivity of the zeolite which ties up the water in the foam.

DETAILED DESCRIPTION OF THE INVENTION

The products of this invention can be formed in an aerosol container, for example, by forming an emulsion of the propellant in the water with the surfactant at the interface and suspending the zeolite component in the emulsion. The zeolite acts as an adsorbant of the propellant and the water. The subject composition comprises the following four essential components:

| Component | % w/w |
|---|---|
| zeolite | 14–40 |
| surfactant | 0.5–13 |
| water | 32–55 |
| propellant | 10–35 | within the following critical ranges:

| | Ratios |
|---|---|
| zeolite:surfactant | 1:0.035 to 1:0.65 |
| zeolite:water | 1:1 to 1:1.275 |
| zeolite:propellant | 1:0.43 to 1:1.16 |

It will be understood that these are the components and ratios required for providing the foamed aerosol composition characterized by the pronounced dryness effect upon discharge from the aerosol container and that the basic foamable composition may have added thereto an active or inactive ingredients which do not adversely affect the foam and its dryness characteristic, so as to produce a wide and varied range of products such as, for example, hair care products, skin care products, e.g., deodorants, antiperspirants, anti-acne products, after shaving talcs, makeup foundation bases and the like, and other cosmetic, household, industrial, pharmaceutical and the like products wherein the utilization of a dry aerosol is deemed suitable. The examples of such foam products given hereinafter are merely exemplary of such products and in no way restrictive of the type and nature of such desired foam products.

Molecular sieves or zeolites used in the compositions of this invention are crystalline aluminosilicates materials of the following general formula

$$M_{2/n}O.SiO_2.aAl_2O_3.bH_2O$$

in the salt form where M is a metal cation, ordinarily Na or K but may be other cations substituted by exchange such as calcium or the like, n is the valence of the metal cation, a is the number of moles of alumina and b is the number of moles of hydration.

Molecular sieves or crystalline aluminosilicates are also sometimes referred to as crystalline zeolites and are of both natural and synthetic origin. Natural crystalline aluminosilicates exhibiting molecular sieve activity include for example, analcite, paulingite, ptilolite, clinoptilolite, ferrierite, chabazite, genclinite, levynite, erionite and mordenite.

Since not all of the natural crystalline aluminosilicates are available in abundance, considerable attention has been directed to the production of synthetic equivalents. Two basic types of crystalline aluminosilicate molecular sieves most readily available on a commercial scale have been given the art-recognized designations of "Zeolite X" and "Zeolite A". Other molecular sieves which have been synthesized include Zeolites, B, F, G, H, K-G, J, L, M, K-M, Q, R, S, T U, Y and Z.

Such molecular sieves or zeolites are described more fully in U.S. Pat. Nos. 3,888,998 and 4,007,134, incorporated herein by reference thereto. More particularly, Zeolite X and Zeolite A and processes for thweir preparation are described in U.S. Pat. Nos. 2,882,244 and 2,882,243 respectively, both incorporated herein by reference thereto. The zeolite used in the compositions of this invention may be activated zeolites, that is, dehydrated, or hydrous at a level of about 16–34% w/w water. The indicated amount of zeolite in the subject compositions, i.e., 14–40% w/w, refers to the activated forms of zeolite. If hydrous zeolite is used, the water vehicle content in the composition should be appropriately compensated.

A wide variety of liquified gases may be employed as the propellant in the crackling foam compositions of this invention. Such liquified gases are liquified hydrocarbon gases and fluorinated hydrocarbons. As examples of such liquified gases there may be mentioned, for example, fluorinated hydrocarbons such as octafluorocyclobutane (FREON C-318), monochloropentafluoroethane (FREON-115), chlorodifluoromethane (FREON-22), dichlorodifluoromethane (FREON-12), 1,2-dichloro1,1,2,2-tetrafluoroethane (FREON-114), dichloromonofluoromethane (FREON 21), and liquified hydrocarbons such as propane, butane, isobutane, cyclobutane and pentane and the like as well as mixtures of all of such liquified gases.

The surfactant employed in the foam products of this invention can be any suitable amphoteric, polar non-ionic, non-ionic, zwitterionic, anionic and cationic surfactants or a mixture thereof. This ingredient functions as a lathering and also as a cleansing agent.

Anionic surfactants, that may be employed in the compositions of this invention are water-soluble soap, non-soap synthetic surfactants or mixtures thereof.

Suitable non-soap anionic organic detergents include, for example, water-soluble salts of organic sulfuric reaction products having in their molecular structure an alkyl group containing from about 8 to about 20 carbon atoms and a radical selected from the group consisting of sulfuric acid ester and sulfonic acid radicals. Important examples of this type of non-soap anionic synthetic detergent, include the sodium, potassium ammonium, or alkanolamine alkyl sulfates, especially those derived by sulfation of higher alcohols produced by reduction of tallow or coconut oil glycerides; sodium or potassium alkyl benzene sulfonates, especially those of the types described by Guenther et al. in U.S. Pat. No. 2,220,099, granted Nov. 5, 1940 and by Lewis in U.S. Pat. No. 2,477,383, granted July 26, 1949, in which the alkyl group contains from about 9 to about 15 carbon atoms; sodium alkylglyceryl ether sulfonates, especially those ethers of higher alcohols obtained from tallow and coconut oil; sodium coconut oil fatty acid monoglyceride sulfates and sulfonates; sodium salts of sulfuric acid esters of the reaction product of one mole of a higher fatty alcohol (i.e. tallow or coconut oil alcohols) and about 3 moles of ethylene oxide; and others well known in the art, a number being specifically set forth in Byerly, U.S. Pat. Nos. 2,486,921 and 2,486,922.

Additional non-soap anionic organic synthetic detergents which can be used in this invention include the salts of the condensation products of fatty acids with sarcosine, i.e. acyl sarcosinate, wherein the acyl radical has a chain length range from about 10 to 18 carbon atoms.

Preferably, the non-soap anionic organic detergent will be of the high sudsing type as for example, the alkylglyceryl-ether sulfonates, the sulfated fatty alcohols or the alkyl ether ethylene oxide sulfates wherein the ethylene oxide chain averages 3 units, and acyl sarcosinates, all as more fully set forth above. These and the foregoing detergents can be used in the form of their sodium, potassium, ammonium or lower alkanolamine such as triethanolamine salts.

Conventional soaps may also be used as the anionic detergent component of this invention. Suitable soaps include the sodium, potassium, and lower alkanolamine salts of higher fatty acids of naturally occurring vegetable or animal fats and oils. For example, sodium, potassium and triethanolamine salts of fatty acids occurring in coconut oil, soybean oils, castor oil or tallow, or salts of synthetically produced fatty acids may be used.

A preferred anionic surfactant is the triethanolamine salt of coconut fatty acid, since it is more readily soluble than the salts of higher alkyl chain length fatty acids. Other preferred anionic surfactants include the sodium and potassium salts of coconut fatty acid; sodium lauryl diethoxy sulfate; triethanol amine lauryl sulfate and sodium dodecyl sulfate.

Polar non-ionic detergents can be used in compositions of the invention, either by themselves or in conjunction with an amphoteric detergent. By polar non-ionic detergent is meant a detergent in which the hydrophilic group contains a semi-polar bond directly between two atoms, e.g. N→O and P→O. There is charge separation between the two directly bonded atoms, but the detergent molecule bears no net charge and does not dissociate into ions at neutral pH.

Suitable polar non-ionic detergents include open-chain aliphatic amine oxides of the general formula $R_1R_2R_3N{\rightarrow}O$. The arrow is a conventional representation of a semi-polar bond. These compounds are generally prepared by the direct oxidation of the appropriate tertiary amine. When $R_1$ is a much larger chain than $R_2$ and $R_3$, the amine oxides have surface activity. For the purpose of this invention, $R_1$ is an alkyl, alkenyl or monohydroxyalkyl radical having from about 10 to about 16 carbon atoms. Desirable surface active properties are lost if $R_1$ is substantially less than about 10 carbon atoms and the compounds are insufficiently soluble if $R_1$ is greater than about 16 carbon atoms. $R_2$ and $R_3$ are each selected from the group consisting of methyl, ethyl, propyl, ethanol and propanol radicals. Preferably $R_1$ is a dodecyl radical or a mixture of dodecyl with decyl, tetradecyl and hexadecyl such that at least 50% of the radicals are dodecyl radicals. $R_2$ and $R_3$ are preferably methyl radicals. A preferred amine oxide for the purpose of this invention is a dodecyldimethylamine oxide.

Other operable polar non-ionic detergents are the open chain aliphatic phosphine oxides having the general formula $R_1R_2R_3P{\rightarrow}O$, wherein R is an alkyl, alkenyl or monohydroxyalkyl radical ranging in chain length from 10 to 18 carbon atoms, and $R_2$ and $R_3$ are each alkyl and monohydroxy-alkyl radicals containing from 1 to 3 carbon atoms. A preferred phosphine oxide is dodecyldimethyl phosphine oxides.

As hereinbefore stated, amphoteric detergents can be used in compositions of the invention, either in conjunction with or in place of the polar non-ionic detergents described above. As used herein, the term "amphoteric" is interchangeable with the term "ampholytic". Amphoteric detergents are well known in the art and many operable detergents of this class are disclosed by A. M. Schwartz, J. W. Perry and J. Birch in "Surface Active Agents and Detergents", Interscience Publishers, New York 1958, Vol. 2. Examples of suitable amphoteric detergents include, for example, alkyl betaiminodipropionates, $RN(C_2H_4COOM)_2$; alkyl betaamino propionates, $RN(H)C_2H_4COOM$; and long chain imidazole derivatives having the general formula:

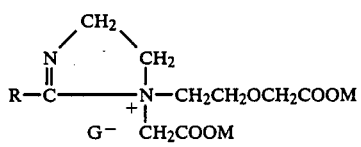

In each of the above formulae R is an acyclic hydrophobic group containing from about 8 to about 18 carbon atoms; G is a hydroxyl, chloride, sulfate or surface active sulfate or sulfonate group and M is a cation to neutralize the charge of the anion. Specific operable amphoteric detergents include the disodium salt of lauroylcycloimidinium-1-ethoxyethionic acid-2-ethionic acid, dodecyl beta alanine, and the inner salt of 2-trimethylamino lauric acid. The substituted betaines and sultaines, such as alkyl ammonio acetates wherein the alkyl radical contains from about 12 to 18 carbon atoms can also be used. The betaine and sultaine types of ampholytic detergents are zwitterionic quaternary ammonium compounds having a general formula:

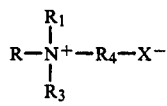

wherein $R_1$ is an alkyl having from about 10 to about 18 carbon atoms, $R_2$ and $R_3$ are each alkyl having from about 1 to about 3 carbon atoms, $R_4$ is an alkylene or hydroxyalkylene having from 1 to 4 carbon atoms, and X is an anion selected from the group consisting of $-SO_3^-$ and $-COO^-$.

Compounds which conform to the above general formula are characterized by the presence of both positive and negative charges which are internally neutralized (i.e. zwitterionic). When the anion X is $-SO_3^-$, the compounds are referred to as "sultaines". The term "betaines" is employed when the anion X is $-COO^-$. The following structural formulae are illustrative of the two types and their inner salt character (a=3).

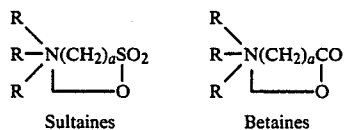

When one R in the above formulae is a high weight alkyl having from about 10 to 18 carbon atoms, these compounds are surface active and have good detergency powers. If the high molecular weight alkyl contains less than about 10 carbon atoms, surface activity and detergency are inadequate. If this group contains more than about 18 carbon atoms, the compounds are not sufficiently soluble to be of utility in this invention. Preferably, the high molecular alkyl will contain from 12 to 16 carbon atoms or a mixture of dodecyl with decyl, tetradecyl, and hexadecyl radicals. A convenient source of a suitable mixture of alkyl groups is the middle cut of coconut fatty alcohol which has the approximate chain length composition: 2%—$C_{10}$, 66%—$C_{12}$, 23%—$C_{14}$, and 9%—$C_{16}$. Particular advantage can be gained by employing betaine or sultaines having an alkyl containing 16 carbon atoms in the compositions of this invention. The alkyl can, of course, contain one or more intermediate linkages such as ether or polyether linkages or non-functional substituents such as hydroxyl or halogen which do not substantially affect the hydrophobic character of the group.

Preferred compounds which fall within the above class include 1-(alkyldimethylammonio)acetate, 1-(alkyldimethylammonio)propane-3-sulfonate and 1-(alkyldimethylammonio)-2-hydroxy-propane-3-sulfonate wherein the alkyl contains from 12 to 16 carbon atoms.

Especially preferred surfactants for use in the foam compositions of this invention are nonoxyl 6 phosphate as an anionic surfactant, isotearamide DEA as non-ionic surfactant, cocaimidopropyl betaine as an amphoteric surfactant and dodecylbenzyltrimonium chloride as a cationic surfactant.

As indicated earlier in order to produce any specific type of foam aerosol product according to this invention the foam composition of this invention can have added thereto any active or inactive ingredients for such type of product and which do not unduly adversely affect the foam and dryness characteristics of the basic compositions of this invention.

The following are examples of typical product application of the aerosol foam compositions of this invention. It will be appreciated that these examples are merely illustrative and not limiting of the many possible product applications of such foam compositions. In the example the percentage and parts are expressed as percent by weight and parts by weight.

EXAMPLE 1

After Shave Talc

Eighty parts by weight of an after shave talc composition comprising:

|  | % w/w |
| --- | --- |
| nonoxynol 6 phosphate | 3.0 |
| sodium A zeolite | 25.0 |
| talc | 20.0 |
| fragrance | 2.0 |
| water | 50.0 | is pressurized in an aerosol container with 20 parts by weight of isobutane propellant to produce a foamable product of the following composition:

|  | % w/w |
| --- | --- |
| nonoxynol 6 phosphate | 2.4 |
| sodium A zeolite | 20.0 |
| talc | 16.0 |
| fragrance | 1.6 |
| water | 40.0 |

|  | % w/w |
|---|---|
| isobutane | 20.0 |

Upon discharge of this product from the aerosol container, the composition produces a light fluffy foam with a dry feel and can be used as an after shave talc. By spreading the foam evenly on the shaved skin surface, a dry film of powder is deposited.

EXAMPLE 2

Anti-Acne Foam

Eighty parts by weight of an anti-acne foam composition comprising:

|  | % w/w |
|---|---|
| nonoxynol 6 phosphate | 3.0 |
| benzoyl peroxide | 2.5 |
| dehydrated sodium A zeolite | 30.0 |
| iron oxides | 0.4 |
| lactic acid | 3.5 |
| water | 60.6 | ps is pressurized in an aerosol container with 20 parts by weight of isobutane propellant to produce a foamable product of the following composition:

|  | % w/w |
|---|---|
| nonoxynol 6 phosphate | 2.4 |
| benzoyl peroxide | 2.0 |
| sodium A zeolite | 24.0 |
| iron oxides | 0.32 |
| lactic acid | 2.8 |
| water | 42.48 |
| isobutane | 20.0 | p The benzoyl peroxide is the active anti-acne ingredient. The iron oxides are added as colorants and the lactic acid is used for pH adjustment. Upon discharge of this product from the aerosol container, the composition produces a light, dry, fluffy foam which can be used on skin afflicted with acne.

EXAMPLE 3

Deodorant

Eighty parts by weight of a deodorant foam composition comprising:

|  | % w/w |
|---|---|
| nonoxynol 6 phosphate | 3.0 |
| sodium A zeolite | 30.0 |
| triclosan | 0.75 |
| talc | 10.0 |
| fragrance | 0.25 |
| water | 56.0 | is pressurized in an aerosol container with 20 parts by weight of isobutane to produce a foamable product of the following composition:

|  | % w/w |
|---|---|
| nonoxynol 6 phosphate | 2.4 |
| sodium A zeolite | 24.0 |
| triclosan | 0.6 |
| talc | 8.0 |
| fragrance | 0.2 |
| water | 44.8 |
| isobutane | 20.0 |

The triclosan, chemically denoted as 2,2,4'-trichloro-2'-hydroxy diphenyl ether, is the active deodorant ingredient. The talc ingredient provides slip. Upon discharge of this product from the aerosol container, the composition produces a dry foam which can be applied to the skin as a deodorant.

EXAMPLE 4

A similar after shave talc dry foam is produced when the 20 parts isobutane propellant of Example 1 is replaced with 20 parts of a 20:80 mixture of tetrafluorodichloroethane and dichlorodifluoromethane propellant, or 20 parts of butane propellant, or 20 parts of a propane/isobutane mixture (16/84) propellant.

EXAMPLE 5

A similar anti-acne dry foam is produced when the dehydrated sodium A zeolite of Example 2 is replaced with an equivalent amount of hydrated sodium A zeolite.

EXAMPLE 6

When the monoxynol 6 phosphate anionic surfactant of the composition of Example 3 is replaced with an equivalent amount of isostearamide DEA nonionic surfactant, or dodecylbenzyltrimonium chloride cationic surfactant, or cocamidopropyl betaine amphoteric surfactant, a similar foamable composition is obtained producing a dry deodorant foam.

EXAMPLE 7

Makeup Foundation Foam

Eighty parts by weight of the following tabulated composition is pressurized in an aerosol container with 20 parts by weight of isobutane propellant to produce a foamable makeup foundation composition.

|  | % w/w |
|---|---|
| monoxynol 6 phosphate | 2.0 |
| sodium A zeolite | 35.0 |
| iron oxides | 8.0 |
| titanium dioxide | 2.0 |
| talc | 1.0 |
| water | 52.0 |

The resultant foam provides a light, airy, makeup foundation base which spreads evenly and smoothly on the skin surface.

EXAMPLE 8

Body Talc

Eighty parts by weight of the following tabulated composition is pressurized in n aerosol container with 20 parts by weight of isobutane propellant to produce a flamable body talc composition.

|  | % w/w |
|---|---|
| sodium cocoyl isethionate | 3.0 |
| sodium A zeolite | 25.0 |
| talc | 30.0 |
| fragrance | 1.0 |

| | % w/w |
|---|---|
| water | 41.0 |

The resultant foamed body talc can be spread easily and evenly on the body. In contrast to conventional sprinkle talc powders, this body talc is neither messy nor does it have airborne particles which can be inhaled.

EXAMPLE 9

The following foamable compositions provide substantially dry to the touch foams in accordance with this invention. The parenthetical numbers show the ratio of zeolite to the respective ingredient.

| Component | % w/w | | | | | |
|---|---|---|---|---|---|---|
| | A | B | C | D | E | F |
| sodium A zeolite | 20.0 | 20.0 | 25.0 | 28.0 | 30.0 | 40.0 |
| water | 55.0 | 45.0 | 43.0 | 51.0 | 42.0 | 40.0 |
| | (1:2.75) | (1:2.25) | (1:1.72) | (1:1.82) | (1:1.4) | (1:1) |
| sodium lauryl sulfate | 3.0 | — | — | 1.0 | — | 3 |
| | (1:0.15) | | | (1:0.035) | | (1:0.075) |
| cocamide DEA | — | 13.0 | — | — | 8.0 | — |
| | | (1:0.65) | | | (1:0.266) | |
| lauramide DEA | — | — | 3.0 | — | — | — |
| | | | (1:0.12) | | | |
| isobutane | 22.0 | 22.0 | — | 20.0 | 20.0 | — |
| | (1:1.1) | (1:1) | | (1:0.714) | (1:0.666) | |
| propane/isobutane (16/84) | — | — | 29.0 | — | — | 17.0 |
| | | | (1:1.16) | | | (1:0.43) |

We claim:

1. An aerosol foamable composition producing a dry foam upon discharge from an aerosol container comprising:
    from about 14 to about 40 percent by weight zeolite;
    from about 0.5 to about 13 percent by weight surfactant;
    from about 32 to about 55 percent by weight water; and
    from about 10 to about 35 percent by weight liquified gas propellant;
wherein:
    the ratio of zeolite to water is from about 1:1 to about 1:2.75;
    the ratio of zeolite to surfactant is from about 1:0.035 to about 1:0.65; and
    the ratio of zeolite to propellant is from about 1:0.43 to about 1:1.16;
said liquified gas propellant being selected from the group consisting of liquified hydrocarbon and fluorinated hydrocarbon gases.

2. The composition of claim 1 wherein the zeolite is sodium A zeolite.

3. The composition of claim 1 wherein the surfactant is a compound selected from the group consisting of nonoxynol 6 phosphate, isostearamide DEA, sodium lauryl sulfate, cocamidopropyl betaine, cocamide DEA, lauramide DEA and dodecyl benzyltrimonium chloride.

4. The composition of claim 1 wherein the liquified gas propellant is selected from the group consisting of butane, isobutane, propane, tetrafluorodichloroethane and dichlorodifluoromethane and mixtures thereof.

5. The composition of claim 2 wherein the surfactant is nonoxynol 6 phosphate and the liquified gas propellant is isobutane.

6. An aerosol foamable composition producing a dry after shave talc foam upon discharge from an aerosol container comprising, in percent by weight:
    about 2.4% nonoxynol 6 phosphate;
    about 20.0% sodium A zeolite;
    about 16.0% talc;
    about 1.6% fragrance;
    about 40.0% water; and
    about 20.0% isobutane.

7. An aerosol foamable composition producing a dry anti-acne foam upon discharge from an aerosol container comprising, in percent by weight:
    about 2.4% nonoxynol 6 phosphate;
    about 2.0% benzoyl peroxide;
    about 24.0% sodium A zeolite;
    about 0.32% iron oxides;
    about 2.8% lactic acid;
    about 42.48% water; and
    about 20.0% isobutane.

8. An aerosol foamable composition producing a dry deodorant foam upon discharge from an aerosol container comprising, in percent by weight:
    about 2.4% nonoxynol 6 phosphate;
    about 24.0% sodium A zeolite;
    about 0.6% triclosan;
    about 8.0% talc;
    about 0.2% fragrance;
    about 44.8% water; and
    about 20.0% isobutane.

9. An aerosol foamable composition producing a dry makeup foundation foam upon discharge from an aerosol container comprising, in percent by weight:
    about 2.0% monoxynol 6 phosphate;
    about 35.0% sodium A zeolite;
    about 8.0% iron oxides;
    about 2.0% titanium dioxide;
    about 1.0% talc;
    about 52.0% water; and
    about 20.0% isobutane.

10. An aerosol foamable composition producing a dry body talc foam upon discharge from an aerosol container comprising, in percent by weight:
    about 3.0% sodium cocoyl isethionate;
    about 25.0% sodium A zeolite;
    about 30.0% talc;
    about 1.0% fragrance;
    about 41.0% water; and
    about 20.0% isobutane.

* * * * *